United States Patent [19]

Hnatow et al.

[11] Patent Number: 5,434,330

[45] Date of Patent: Jul. 18, 1995

[54] PROCESS AND APPARATUS FOR SEPARATION OF CONSTITUENTS OF GASES USING GAS HYDRATES

[76] Inventors: Miguel A. Hnatow, 45 Cedars Rd., Caldwell, N.J. 00706; John Happel, 69 Tompkins Ave., Hasting-on-Hudson, N.Y. 10706

[21] Appl. No.: 81,672

[22] Filed: Jun. 23, 1993

[51] Int. Cl.[6] .............................................. C07C 7/00
[52] U.S. Cl. ..................................... 585/864; 585/866; 95/149; 95/187; 95/199; 95/237
[58] Field of Search ................. 585/864, 866; 95/149, 95/187, 199, 237

[56] References Cited

U.S. PATENT DOCUMENTS

| | | | |
|---|---|---|---|
| 3,977,203 | 8/1976 | Hinton et al. | 62/17 |
| 4,305,733 | 12/1981 | Scholz et al. | 48/196 R |
| 5,047,074 | 9/1991 | MacGregor et al. | 55/48 |

*Primary Examiner*—Anthony McFarlane
*Assistant Examiner*—Nhat D. Phan
*Attorney, Agent, or Firm*—John Q. McQuillan

[57] ABSTRACT

A process and an apparatus for separating desired clathrate forming gases from a gas mixture containing the desired clathrate forming gases. The process includes providing a stream of the gas mixture, contacting the stream of the gas mixture with an aqueous solvent to form a solid clathrate hydrate suspension in the aqueous solvent. The forming of the solid clathrate hydrate suspension in the aqueous solution causing the gaseous stream to be thereafter leaner in the desired clathrate forming gases. The solid clathrate hydrate suspension and the aqueous solution are subjected to an elevated temperature and to a reduced pressure to produce a product gaseous stream which is richer in the desired clathrate forming gases.

29 Claims, 10 Drawing Sheets

EXPERIMENTAL APPARATUS FOR SEPARATION OF NITROGEN FROM METHANE BY HYDRATE FORMATION

PROCESS AND APPARATUS FOR SEPARATION OF CONSTITUENTS OF GASES USING GAS HYDRATES

BACKGROUND OF THE INVENTION

1. Field of the Invention

The invention relates to a process and apparatus for effecting separation of gases which are constituents from other low molecular weight gas mixtures by the controlled formation and decomposition of hydrates of the gases to be separated. The most widely used present technology for such separations is cryogenic distillation which is costly due to the low temperature required to liquefy methane. Other separation processes include gaseous diffusion using membranes and pressure swing adsorption, but these processes generally have not proven to be economical.

2. Description of Prior Art

The term "gas hydrates" has been applied for over a century to the solids that are formed by the combination of a number of gases with water. They constitute a class of solids in which small molecules occupy almost spherical holes in icelike lattices made up of hydrogen-bonded water molecules. Gas hydrates are structural combinations that remain associated not through strong attractive chemical forces but because strong mutual binding of the molecules of water makes possible the formation of cagelike structures that firmly enclose individual gas molecules. These combinations have been termed clathrates to distinguish them from hydrates in which chemical forces result in constant proportions of interacting species in combination with water molecules.

There is a considerable body of research devoted to equilibrium formation of hydrates stemming from the discovery over fifty years ago that blockages in natural gas pipelines exposed to low temperatures were due to formation of gas hydrate rather than of ice. Results of these studies have been summarized in a recent comprehensive treatise (E. Dendy Sloan, Jr., "Clathrate Hydrates of Natural Gases", Dekker N.Y. (1990)). A survey of the many studies of equilibrium properties of natural gas hydrates shows that correlations are adequate for prediction of the conditions that will result in hydrate formation; however, very little data are available on the composition of the hydrates formed. Hydrate compositions have been predicted by means of sophisticated statistical thermodynamic procedures for calculation of hydrate equilibria. Unfortunately, prediction by these procedures leads to conflicting results for the methane-nitrogen system. This problem stems from the unusual behavior of the nitrogen-water system.

Advanced methods of treating hydrate equilibria by statistical thermodynamics depend on microscopic properties of the structures. These crystal structures were studied in some detail in the 1950's by x-ray techniques. It was found that most gas hydrates constitute a class of solids in which small molecules of many types occupy almost spherical holes in ice-like lattices made up of hydrogen-bonded water molecules. The great majority of gas hydrates of pure substances have been shown to conform to either of two forms, designated as Structure I and Structure II respectively. Methane forms Structure I hydrates and until a few years ago it was thought that nitrogen also assumed this form of hydrate; however, it was recently discovered that nitrogen hydrate Conforms to Structure II (Davidson, D. W. et al. Mol. Cryst. Liq. Cryst., 141, 141 (1986)). It is believed that hydrates of gas mixtures will conform to either Structure I or Structure II, but statistical thermodynamic methods differ as to the methane-nitrogen proportions at which the transition occurs as the proportion of methane to nitrogen in a mixture of the two is increased. This is an important factor in determining the feasibility of separating high methane containing gases from such mixtures.

SUMMARY OF THE INVENTION

In accordance with the invention new factors have been determined for controlling the formation and decomposition of gas hydrates that permit surprisingly high separation rates to be attained. Based on these findings, we have demonstrated the elements of a promising technology for effective recovery of methane from sub-specification natural gas containing nitrogen or from methane containing streams diluted with hydrogen and carbon monoxide in coal gasification for synthetic natural gas production.

Because of its important practical value, the nitrogen-methane system was chosen as a model for experimental study. A point of departure for consideration of appropriate conditions required for separation is the behavior of this system under equilibrium conditions. The equilibrium composition of hydrate corresponding to a given gas phase composition represents the separation attained after a long period of time. This presumably represents the separation that might be approached in an efficient contacting stage with a small enough contacting time or reactor size to be economically practical.

It is an object of the invention to use a precooled stream of methanol in water. This saves heat exchanger surface as compared with gas cooling. More importantly it increases the tendency for hydrate formation, thereby contributing greatly to reduction in equipment size.

It is also an object of the invention to use a high methanol concentration of aqueous solvent to enable substantial methane to be dissolved in the solvent as compared with nitrogen, thereby reducing the required solvent circulation if the solvent stream is separately degassed.

It is a further object of the invention to use an external Venturi type eductor. This provides means for introduction of energy necessary for effective mixing without the installation of expensive moving agitator impellers into a necessarily high pressure reactor, thus minimizing the size of the former itself.

DETAILED DESCRIPTION OF THE PREFERRED EMBODIMENTS

Figure 1:
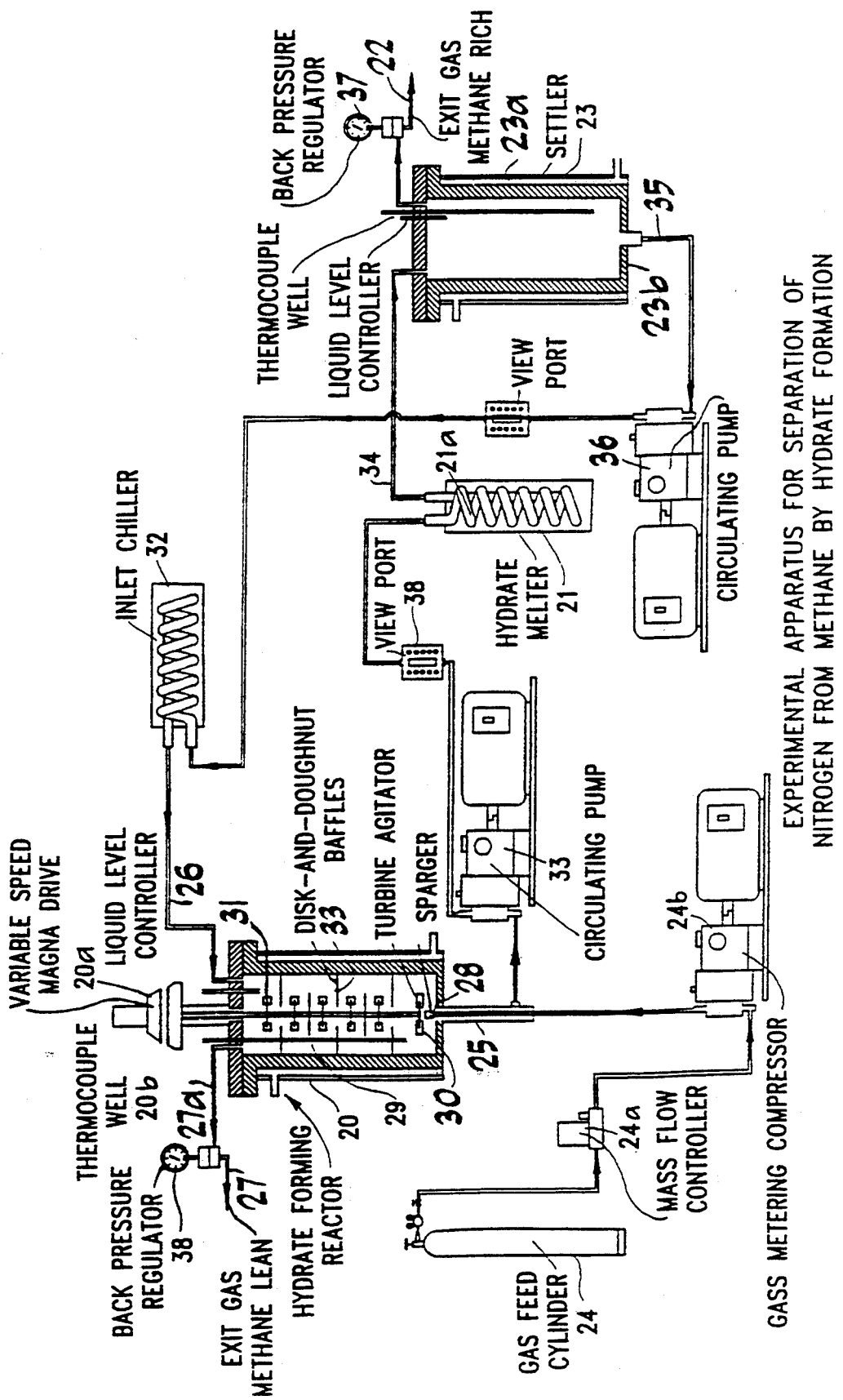
FIG. 1 is a schematic diagram showing the process and apparatus of the invention for separation of a gas constituent from a gas mixture by hydrate formation.

In developing the process of the invention, it was necessary at the outset to experimentally establish the behavior of the nitrogen-methane system under equilibrium conditions. An apparatus was constructed in which it was possible to obtain and analyze samples of the hydrate phase at close to equilibrium conditions. Data can be obtained for a wide variety of mixtures, temperatures, and pressures in which both hydrate and gas phase compositions were determined. Such information over a complete composition range is not presently available. It was determined that gas products could be obtained with a purity exceeding 98% vol. of methane. The results are in approximate agreement with predictions published in Sloan's recent book which does take into account the unexpected existence of Structure II nitrogen hydrate. Other published procedures exhibit greatly varying predictions.

With the theoretical feasibility of separating nitrogen-methane mixtures to produce specification concentrations of methane (over 96%-vol.) established, the next task was to determine whether a workable process could be developed. The capacity of hydrate lattices to encage gaseous molecules is similar to the absorption capacity of activated carbons and zeolites, and the low cost of water as a separating agent is an attractive feature for its use in process applications. It has in fact been proposed (Adamson, A. E., "Physical Chemistry of Surfaces", 3d Ed pp 616–658, 1976 Wiley, N.Y.) to consider clathrates as a special case of persorption. The term persorption is used to describe the situation where the pores of a porous material acting as an adsorbent are small enough to act as molecular sieves. In the case of clathrates, such cages are present but there are no access windows as in the case of zeolites. Consequently, the mechanism of clathrate formation is not completely described by this model.

The kinetics of formation and decomposition of hydrates by Bishnoi and his co-workers are among the very few studies reported in the literature (Englezos, P. et al. Chem. Eng. Sci. 42, 2647 (1987)). These authors viewed hydrate formation as a type of crystallization process in which nuclei are first formed, followed by growth of the initial seed crystals. Their correlations are based on rate of hydrate formation from water after initial formation of nuclei signalled by the appearance of turbidity in the stirred semi-batch reactor used to conduct experiments. The time period of experiments varies between one and three hours; however, the time taken to reach turbidity varies from 6 minutes to 16 hours, depending on reactor pressure. In the continuous type of process in accordance with this invention, it is necessary to make provisions for production of hydrate starting from water or an aqueous solution. Therefore it is not desirable to separate these rate processes of nucleation and growth. Even though Bishnoi and co-workers' studies resulted in empirical correlations of a defined growth rate, it is still not clear how growth of so-called nuclei can occur, if the gas clathrate involves cages without windows following Adamson's theory (which they propose describes the mechanism).

Accordingly, experiments were conducted to determine rates of hydrate formation in a continuous type of contacting apparatus in accordance with the invention involving stages for the simultaneous formation and decomposition of hydrates, not only for fuel gases, but mixtures of methane and nitrogen in order that separation effects could also be observed as well as rates of formation and decomposition. A large number of experiments led to the discovery of the process of the invention that hydration rates orders of magnitude greater than previously reported could be attained by more efficient contacting and the long induction period was not necessary.

The appearance of the hydrate particles formed in accordance with the invention is that of an open type structure rather than the regular shape exhibited by one crystal growth. Thus growth consists of agglomeration or aggregation of hydrate cells, rather than initiation of nuclei followed by increase in individual crystal size by further progress of the clathration encaging process at the initial sites. This type of growth is similar to growth patterns of colloidal solutions. It does not involve access of gas molecules into previously formed hydrate cells.

The decomposition of a hydrate suspension by heating does not necessarily involve a direct reversal of the hydrate forming process. There is some evidence of solid interaction as judged by the more regular shape of partially melted or decomposed hydrates. Partially decomposed hydrates are also richer in methane, the less volatile component in methane-nitrogen mixtures.

Of practical importance is the fact that the decomposition of the cell structure results in the re-formation of exceedingly small bubbles as evidenced by the turbidity of the decomposed suspension. The solid hydrate particles are also very small and their density is close to that of ice so that settling from water is slow. These considerations led us to the conclusion that, if possible, physical phase separation steps involving the hydrate suspension should be avoided.

An important practical requirement of the process of the invention is the need to supply sufficient cooling to abstract the heat necessary for hydrate formation from the gaseous feed stream. Experimental data obtained indicated that the ice point (temperature at which ice forms) is considerably lower than that required for hydrate formation, if a methanol-water solution is employed rather than pure water in the former. Use of such a solution avoids the necessity of providing an internal cooler for the former. Hydrate formation using such a solution is still very rapid, provided that sufficient water is present to provide for that required in the formed hydrate.

Thus a continuous process for the separation of methane and other hydrate forming components from natural gas or synthesis gas according to this invention consists of one or more stages that each comprise two essential elements as shown in FIG. 1: a former 20 and a hydrate melter 21 respectively. Optionally a third element consisting of a counter-current contactor of gas and hydrate suspension may be additionally employed in conjunction with the former 20-melter 21 combination. In all cases the process will produce a methane containing product stream of at least 95% vol. methane content, as demonstrated at exit 22 of settler 23 from equilibrium data obtained.

The former 20 produces a hydrate suspension containing crystals of hydrate. The content of the suspended crystals formed is substantially higher in methane content than the feed gas stream from gas feed cylinder 24 which is connected by inlet 25 to former 20. This suspension is formed by feeding a methane containing stream to the former 20. Additionally an aqueous stream is fed to the former 20 by line 26 to provide water for hydrate formation. The aqueous stream may itself contain a substance such as methanol capable of dissolving methane in preference to other components to be rejected, particularly nitrogen or carbon monoxide. In this way a suspension is produced in the former 20 which contains a higher concentration of methane in both solid and liquid phases relative to the gaseous stream leaving the former 20 at line 27.

Figure 2:
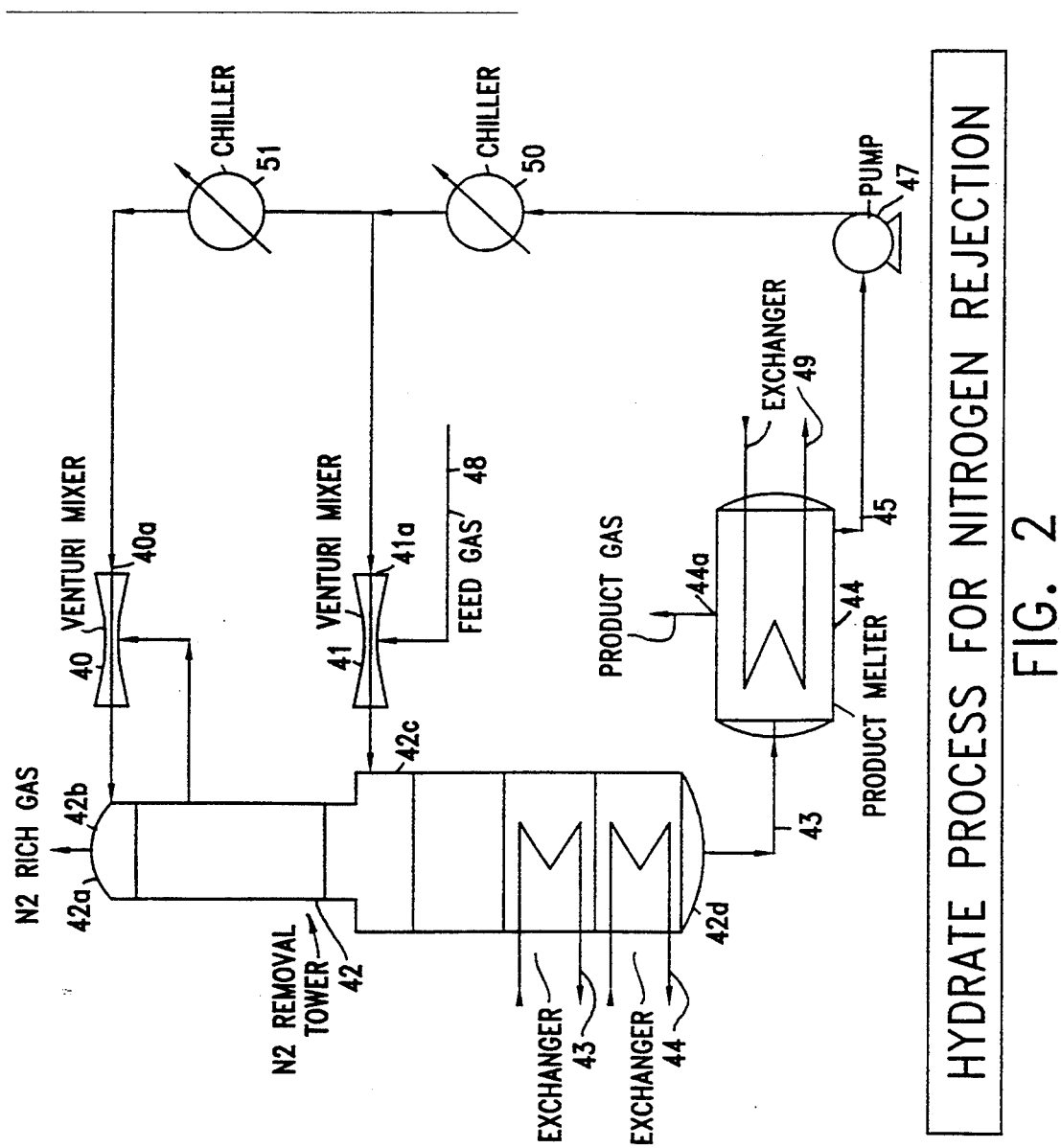
FIG. 2 is a schematic diagram showing other embodiments of the process and apparatus of the invention for separation of a gas constituent from a gas mixture.

Various types of contacting equipment may be used in the former 20. Included are spargers 28, porous tubes and drilled pipes 29, turbine-type mixers 30 and Venturi eductors. When gas is introduced into a former 20 in finely divided bubbles, such as in stirred vessels, it is necessary to provide gas dispersion by means of rotating impellers 31. As shown in FIG. 2 Venturi mixers 40 and 41 are especially advantageous to use for hydrate forming because the aspirated entering gas produces a high interfacial contact area both by liquid and gas phase subdivision in removal tower 42.

An additional requirement for the former 20 of FIG. 1 is the introduction of the aqueous feed at a temperature lower than that required to form hydrate in order to abstract the heat liberated during hydrate production, but still high enough to avoid ice formation in the aqueous solvent before it enters the former 20. Inlet chiller 32 provides the function. Methanol solutions are especially advantageous for this purpose.

After leaving the former 20 the suspension containing hydrate is delivered by circulating pump 33 to the hydrate melter 21 to decompose the solid hydrate by raising its temperature and to release additional dissolved methane rich gas. This process may be facilitated by reduction of pressure. These procedures serve to separate the methane rich product gas.

Operation of the former 20 and melter 21 in conjunction may serve as a single stage of gas processing. Such stages may be operated in sequences in order that a progressively higher methane content is produced at exit 22, by successive treatment of the product from a series. Alternatively, as used in the art of distillation, stages of contacting may be conducted in a single tower 42 as shown in FIG. 2. The use of heating coils of heat exchangers 43 and 44 at the bottom of such a tower 42 is used to produce vapors by a combination of hydrate melting and solvent boiling, while at higher points in the tower 42, hydrate is formed using forming equipment to contact entering solvent streams. Such towers 42 may contain packing or baffles such as baffles 33 in former 20 of FIG. 1. It is possible to operate without such internal means of contacting vapor and the downward moving hydrate suspension since the suspension contains particles which themselves can serve as the equivalent of packing. The liquid leaving such a tower 42 at exit 43 as shown in FIG. 2 passes to a melter 44 to produce a gaseous product stream at exit 44a and aqueous solution at exit 45 for recirculation by pump 47.

Sub-specification natural gas has a lower heating value than specification gas which is caused by the presence of either carbon dioxide and/or nitrogen. The Gas Research Institute (Energy and Environmental Analysis), Inc., "Chemical Composition of Discovered and Undiscovered Natural Gas in the Lower 48 United States", GRI Report 90/0248, GRI Contract #5088-22-1753, July 1991) reports that the concentration of nitrogen in natural gas varies from 5 to 63 mole % for gases associated with oil production and from 5 to 84 mole % for non-associated gas reservoirs. Gases containing more than 4 mole % nitrogen are considered sub-specification and require some processing before introduction into most pipelines. The reserve (current, expected, new potential) are estimated to consist of 54,500 billion cubic feet (BCF) of natural gas. Of this total, 55.7% contain between 5 and 10% by volume nitrogen, 7.0% between 10–15% by volume nitrogen, and 34.3% between 15–30% by volume nitrogen.

Although methane is the predominant component of natural gas, a number of higher molecular weight paraffin hydrocarbons are present in decreasing proportions, ethane, propane, and butanes. The pentane and higher molecular weight hydrocarbons do not form hydrates. The acid gases carbon dioxide and hydrogen sulfide are generally removed by absorption in alkaline media. They form hydrates readily and would be concentrated in the methane rich product stream in the operation of the process of the invention under conditions for nitrogen-methane separation, if they were present in the feed. This would reduce the necessary size of equipment of the invention required for acid gas removal.

Another application of hydrate separation technology is the separation of methane from hydrogen and carbon monoxide. The separation problem is similar to the separation of nitrogen from methane and since hydrogen does not form a hydrate it is released in the carbon monoxide rich effluent stream. The hydrate forming properties of carbon monoxide are similar to those for nitrogen. Davidson et al (Letters to Nature 328, 419, Jul. 30, 1987) report data on the water-carbon monoxide system. The tendency for carbon monoxide to form hydrates is close to that for nitrogen.

Figure 4:
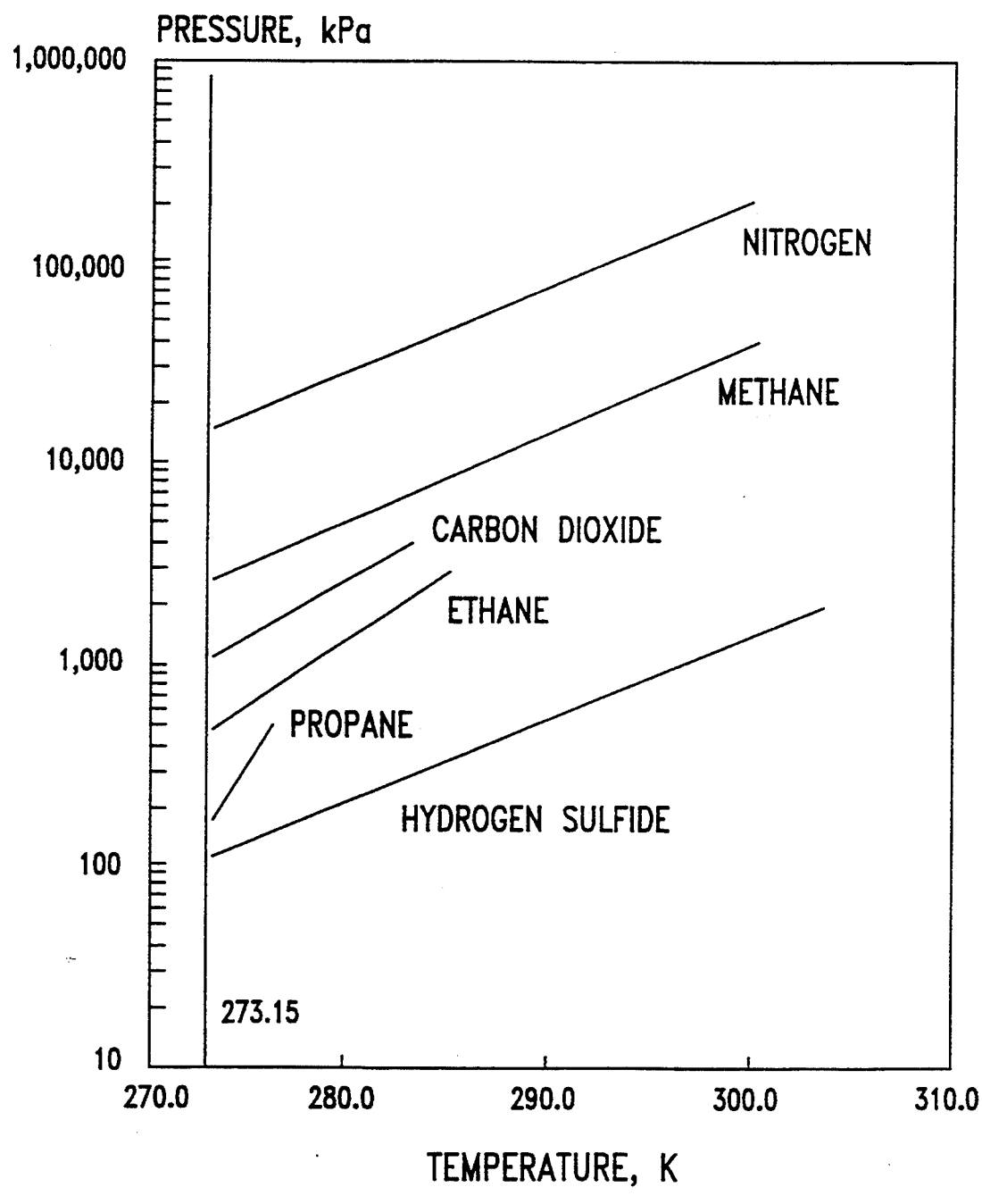
FIG. 4 is a plot of hydrate forming conditions for gases in the presence of water.

FIG. 4 shows the pressure for hydrate formation for these gases vs. temperature. The gases that form hydrates more readily than methane could be concentrated in the methane rich product stream in the operation of the subject process under conditions for nitrogen-methane separation or alternatively could be further separated in the order of their ease in forming hydrates.

In the embodiment of FIG. 1, the liquid leaving former 20 is delivered by circulating pump 33 to hydrate melter 21 to produce a flow gas from exit 34 to settler 23. The aqueous solution at exit 35 is recirculated by circulating pump 36 to inlet chiller 32 and then to former 20.

The separation problem for synthetic natural gas involves carbon monoxide and methane as the key components. The hydrate forming properties of carbon monoxide are similar to those for nitrogen. Hydrogen does not form a hydrate and therefore is released in the carbon monoxide rich effluent stream.

An advantage in using the present process of the invention for upgrading methane containing streams is that separation stages can be arranged so as to remove clathrate formers such as C-2 to C-4 hydrocarbons and thereby reduce the necessity for special addition of chemicals to prevent pipeline plugging.

Carbon dioxide is commonly used in enhancing oil recovery processes. When introduced into a well, the resultant gases associated with the oil production are sub-specification natural gas containing large quantities of carbon dioxide. Hydrate separation technology similar to that developed for nitrogen removal can be applied for the separation of carbon dioxide from methane in such gases.

In general, hydrate forming gases can be separated from either mixtures of gases containing hydrate and non-hydrate forming gases, or from other hydrate forming gases in the order of relative volatility in forming hydrates as given in FIG. 4.

The apparatus of the invention shown in FIG. 1 was used to obtain data on hydrate formation and melting. The apparatus of FIG. 1 embodies a continuous unit including the single former 20 and the melter 21 for single-stage contacting of appropriate gas mixtures containing nitrogen and methane. In this apparatus the feed gas is separated in a single-stage into higher and lower methane content streams.

The apparatus of FIG. 1 includes a gas feed monitoring and delivery system of mass flow controller 24a and gas metering compressor 24b, a hydrate forming reactor or former 20, hydrate melter 21 and gas separation equipment or settler 23, and provisions for monitoring temperatures, pressures, and exit gas flow rates the latter by back pressure regulators 37 and 38. Magnetic drive pumps are used to transport the hydrate slurry and liquid from one unit to the other.

The feed gas was supplied by Matheson Gas Inc. in high pressure cylinders, either pre-mixed or as pure methane or nitrogen and is of research quality. The flow rates of the gases are metered by Brooks mass flow controllers at 250 psig and then compressed to desired reactor pressure by a Whitey metering compressor. The gas is introduced directly near the impeller region in the reactor.

One vent stream leaves the forming reactor through a back pressure regulator that is used to maintain system pressure. A wet test meter is used to monitor the exit flow rate. The gas stream which leaves the melter section 21 is handled in similar fashion. Gas samples are taken and are analyzed using a gas chromatograph.

By way of example, the hydrate forming reactor vessel a one liter, jacketed, high pressure reactor assembly 20 can be equipped with a packless, bolted stirring head and is driven by a variable speed electric motor (not shown). A turbine type impeller 30 is used to promote efficient contact between gas and liquid. The vessel 20 is equipped with a baffles 33 to avoid formation of vortices. The reactor 20 is fitted with a thermocouple well 34b that holds three thermocouples (not shown). All monitor the temperature profile in the vessel 20. A demister (not shown) can be used to separate entrained liquid from the exiting gas stream. Ethylene glycol coolant is circulated through the jacket of reactor 20 to assure controlled temperature operation.

The hydrate containing liquid is pumped from the bottom of the reactor 20 using a metering magnetic drive gear pump 33. The exit stream flows counter-current to the gas flow, minimizing entrainment of gas into the exiting stream. A view port 38 is used to visually inspect the hydrate liquid stream and also provides means for obtaining a hydrate sample for analysis. The stream then enters the hydrate melter 21-gas separation section consisting of a refrigerated bath containing a coiled heat exchanger 21a which is used to melt the hydrate, followed by a one gallon jacketed, high pressure vessel that serves as the settler 23. The settler 23 is packed with extended metallic strips with sharp edges to form sites for bubble nucleation so as to minimize supersaturation of dissolved gases in the aqueous phase. Ethylene glycol coolant is circulated through the jacket 23a of the settler 23 to maintain it under controlled operation close to an adiabatic condition.

The liquid is pumped from the bottom 23b of the settler 23 using a metering magnetic drive gear pump 36. A view port 39 at the exit of the pump is used to visually inspect the liquid stream and provides a means of obtaining a sample of liquid. The liquid then passes through a chiller 23 which cools the liquid to the desired temperature for recycling into the hydrate forming reactor or former 20.

Very little information is available on the rate of hydrate formation. The only kinetic studies of methane hydration suitable for purposes of the invention are those conducted by Bishnoi and his co-workers (Englezos, et al. Chem. Eng. Sci. 42, 2647 (1987)). In order to form a baseline, experiments were conducted studying hydrate formation of methane and with water. Only the forming part of the test unit of FIG. 1 described above was used in these studies. The hydrate containing liquid exiting the view port is sent directly to the chiller 32 which cools the liquid to the desired temperature for recycle into the hydrate former system 20. In both Bishnoi's and the apparatus of the invention, hydrates are accumulated batch-wise. Bishnoi fed gas into the reactor to maintain system pressure and determined the rate of hydrate formation by measuring the rate of uptake of gas. In accordance with the invention, the gas feed is continuous and the rate of hydrate formation is determined by the difference between the inlet and exit flow rates. With pure gases both types of apparatus should yield comparable results for measuring the rates of hydrate formation.

The hydrate forming section of the test unit of FIG. 1 is used to determine how closely the operation of the equipment can approach the thermodynamic equilibrium condition for hydrate formation. A series of experiments have been conducted using pure methane to check thermodynamic equilibrium for methane hydrate formation from water.

Start up of the test unit of FIG. 1 consisted of the following steps: setting the temperature of chiller 32, pressuring the back pressure regulator 38 for the desired operating pressure, filling the unit with distilled water and starting circulation of the liquid phase at a rate of 2 liters/min. After a period of time when the unit reaches a steady state, methane gas is fed to the hydrate former unit 20 at a rate determined by the setting of the mass flow controller 24a. The gas compressor 24b is turned on and the system is pressurized to the desired operating pressure. After stead-ystate is reached, the exit gas flow is measured using a wet test meter. An experiment is started when a balance between the inlet flows and exit flows occur. Experimental observations begin when the speed of impeller 31 has been increased to 2,250 rpm.

One type of experiment is designed to determine equilibrium conditions for methane hydrate formation. The system is pressurized to 800 psia and the reactor former 20 temperature is held constant at about 3.8° C. Hydrate formation in the view port 38 is observed almost immediately. After a period of operation, the methane feed to the former 20 is turned off and the system is allowed to reach an equilibrium condition, maintaining the temperature constant while allowing the pressure to decrease as hydrate formation occur. After a short period of time the pressure drops to 544 psia and remains at this pressure. This pressure corresponds to an equilibrium temperature of 3.8° C. The temperature of the hydrate former 20 is then increased very slowly and the corresponding pressure is observed as the decomposition of hydrate occurred. Data are taken until all of the hydrate is melted.

A second type of experiment is conducted to determine how rapidly methane hydrate can be formed close to equilibrium conditions. A typical dynamic experiment of this type is performed in which 900 cc(NTP)/min of methane is introduced into the hydrate former 20 which is maintained at 4.6° C. and 800 psia. It is impossible to maintain a pressure of 800 psia after about 1 min of operation since the rate of hydrate formation exceeds the feed rate. Since the equilibrium temperature for methane hydrate formation at 800 psia is 7.4° C. the reactor is supercooled by 2.8° C. After operation for a period of 10 to 15 min., the pressure fails to a steady value of 720 psia which corresponds to an equilibrium temperature of 6.3° C. Under this condition the supercooling is 1.7° C. and a steady state consumption of 900 cc(NTP)/min per liter of reactor is reached.

Using these procedures data were taken using pure methane to determine the equilibrium condition for hydrate formation and the rate of pure methane hydrate formation as the degree of supercooling increased. FIG. 2 shows a plot of the experimental data obtained on methane hydrate equilibrium and a comparison with published data (Jhaveri, J., and Robinson, D. B., Can. J. Chem. Eng., 43, 75 (1965) and Deaton, W. M. and Frost, E. M., US Bureau of Mines Monograph 8, 1946. A good agreement was achieved. Data on the rate of methane hydrate formation at various degrees of supercooling are presented in Table 1. Also presented are data reported by Bishnoi and co-workers (Vysniauskas, A. and Bishnoi, P. R., Chem. Eng. Sci. 38, 1061 (1983) and Knox and co-workers (Knox, H. C., Hess, M., Jones, G. E., Smith, H. B., Chem. Eng. Prog. 57, 66 (1961). A maximum rate of hydration was 4,724 cc(NTP)/min per liter of reactor. This corresponds to a rate per unit volume of reactor almost 50 times as fast as that reported by Bishnoi and co-workers. The stirrer in their apparatus was operated at 400 RPM in order to avoid vortex formation. In the apparatus of the invention, the stirrer was operated at 2,250 RPM and baffles 33 were used to prevent vortex formation.

A point of special interest is the fact that previous authors reported that substantial delay occurs before the liquid phase exhibits translucence or turbidity due to sudden emergence of hydrate particles. Bishnoi et al. observed that the time to reach turbidity varied from about 6 min for a high pressure experiment to about 16 hrs. for a low pressure one. Their kinetic correlation of data is based on the rate of hydrate formation after the initial period when hydrate formation was first observed. Uncorrelated induction times could furnish a great obstacle to successful application of these correlations to reactor design. In experiments with this type of apparatus, there is no evidence of delay times exceeding several minutes for appearance of hydrate aggregates. These examples show that the apparatus of the invention can be used obtain both thermodynamic as well as approximate rate data. Equilibrium conditions can be approached quickly and high rates of hydrate formation can be achieved with pure methane.

With pure methane it is possible to show hydrate formation tendency by plotting temperature versus pressure. When an additional component such as nitrogen is added the temperature of hydrate formation at a given pressure will depend on the composition of the gas. It is convenient to represent the data obtained with mixtures in form of plots of composition versus temperature at constant pressure.

Experiments were performed with mixtures of nitrogen and methane. Thermodynamic equilibrium studies were first conducted to a determine phase diagram for the methane-nitrogen system in the gas-hydrate-water region at various pressures and temperatures above the ice point of water. There are considerable thermodynamic data available in the literature to predict the conditions for hydrate formation for a given gas mixture at a specified temperature and pressure. Practically no data are available in which actual hydrate compositions in equilibrium with the vapor phase were determined. While this data base is satisfactory for predicting plugging conditions in pipelines, it does not furnish suitable data for designing a separation process. The test unit of FIG. 1 was therefore modified by using valves to isolate hydrate samples in the view port 38 for analysis.

Experiments with mixtures of methane-nitrogen employed the same apparatus used of FIG. 1 for the pure methane studies. A similar start up procedure was employed. Nitrogen and methane were metered separately and mixed prior entering the gas compressor 24b. The gas compressor 24b was turned on and the system was pressurized to the desired operating pressure. After steady-state was reached the exit gas was analyzed and metered using a wet test meter. An experiment was started when a balance between the inlet and exit flows occurred. Experimental observations began when the speed of impeller 30 had been increased to 2,250 rpm. Hydrate formation occurred promptly. The exit gas flow rate was monitored and exit gas samples were taken and analyzed at timely intervals. After about 20 minutes following the start of a run, steady-state was reached and a constant exit gas composition was observed. Hydrate samples were then isolated in the view port 39 and the hydrate samples were taken and analyzed. For the given operating temperature and pressure the analysis of the hydrate and exit gas composition were determined. Several such experiments were conducted at successively lower feed rates until no change was observed in the exit vent gas composition. This feed rate was taken as that corresponding to equilibrium. Operating under these conditions, experiments were conducting employing mixtures of nitrogen and methane.

For a typical experiment, a feed gas containing about 64% by volume of methane and 36% by volume of nitrogen was fed into the hydrate former 20 at a rate of 1,666 cc(NTP)/min operating at 820 psia and 3.0° C. At steady state the exit flow was averaged at 1,365 cc(NTP)/min. Thus the rate of hydrate formation was equivalent to 301 cc(NTP)/min. The composition of the vapor phase was 59.7 vol. % methane. The hydrate composition was 84.8 vol. % methane.

Figure 3:
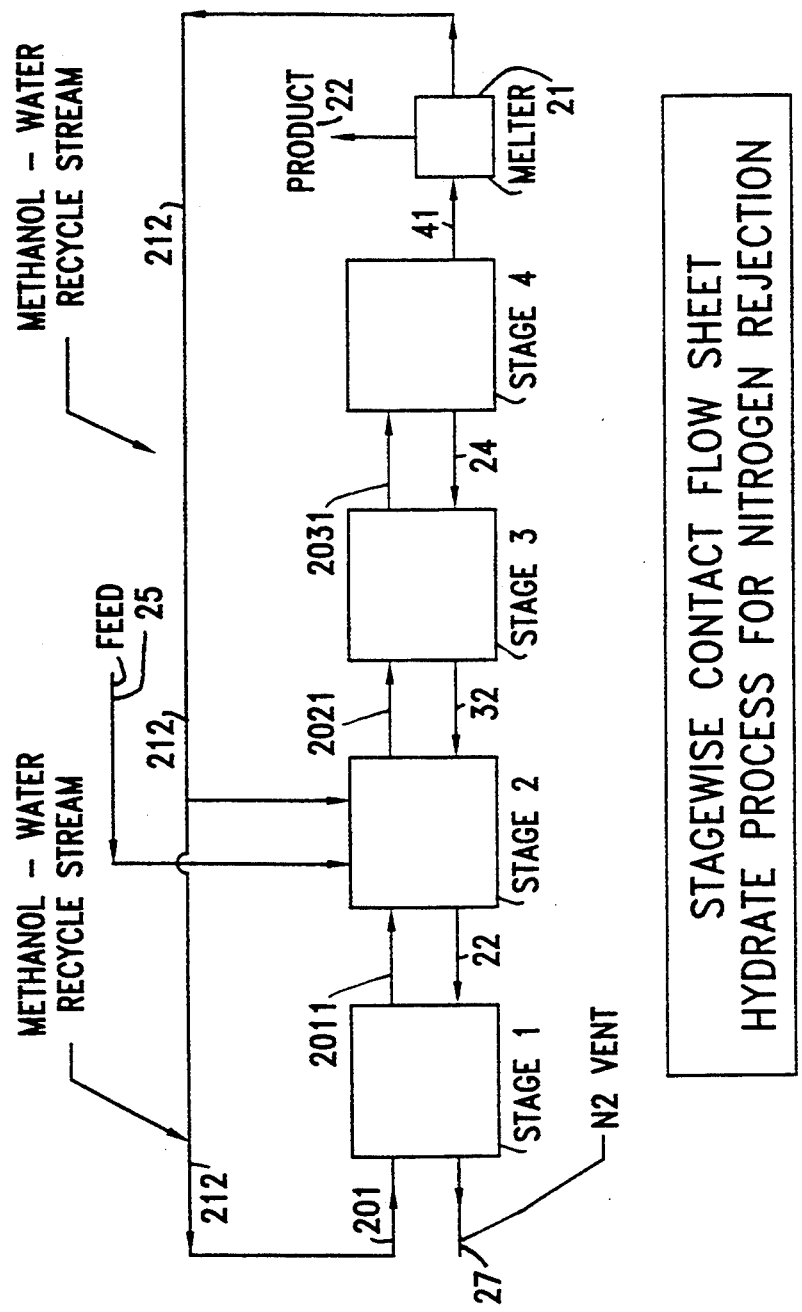
FIG. 3 is a flow sheet of the process of the invention.
Figure 5:
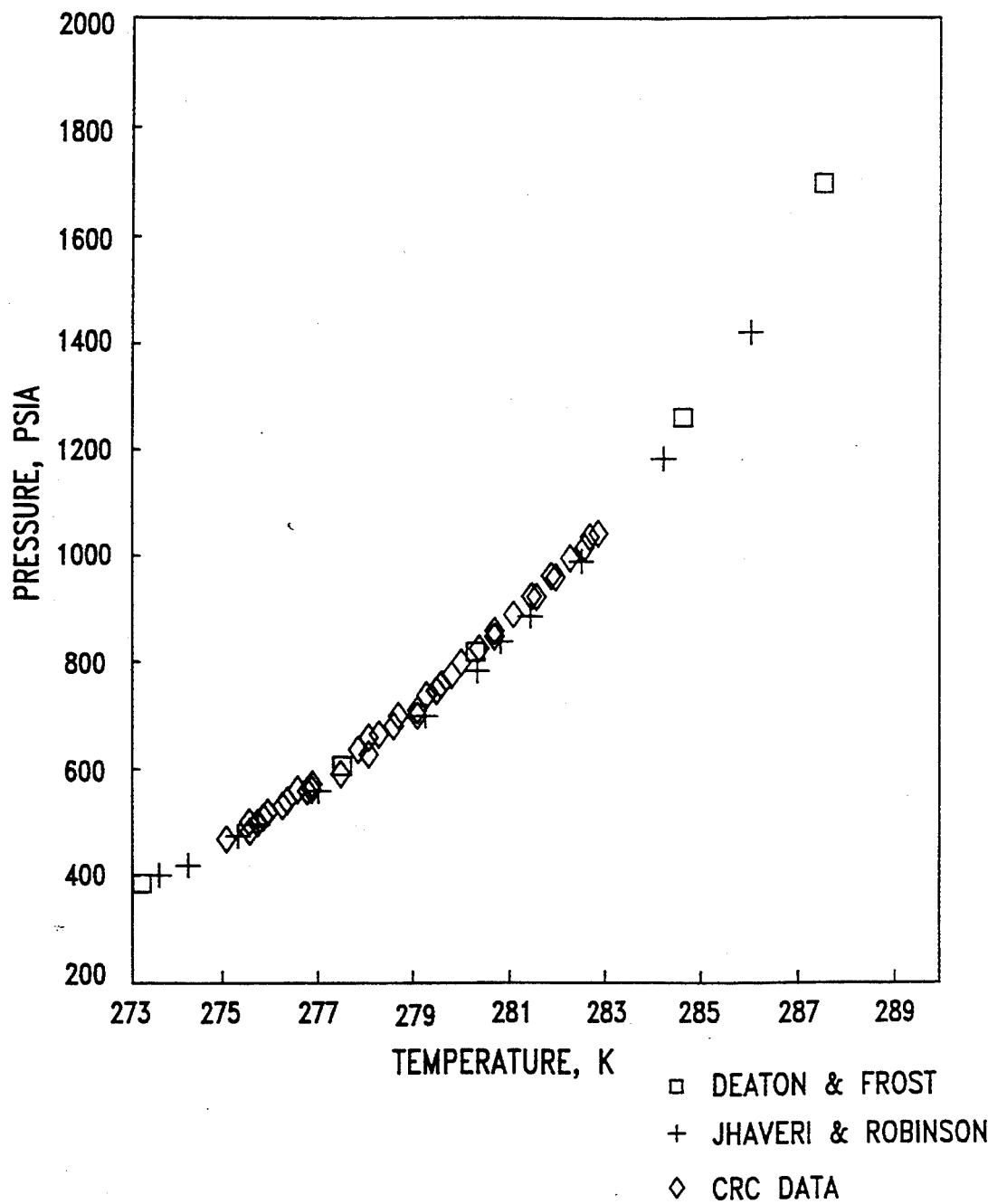
FIG. 5 is a plot of methane hydrate equilibrium data.
Figure 6:
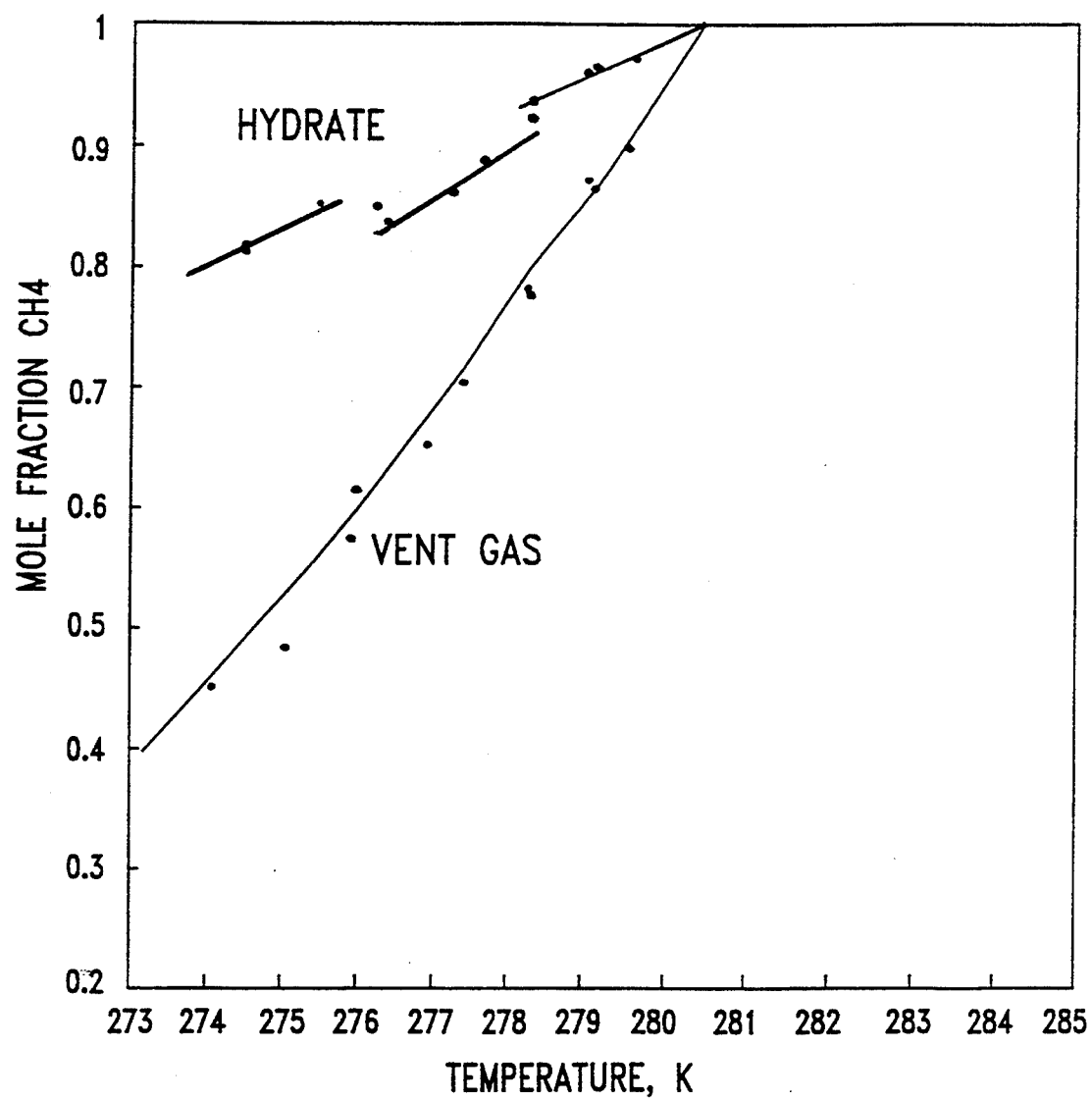
FIG. 6 is a plot of $CH_4$—$N_2$ hydrate equilibrium phase diagram—pressure appx. 820 psia.
Figure 7:
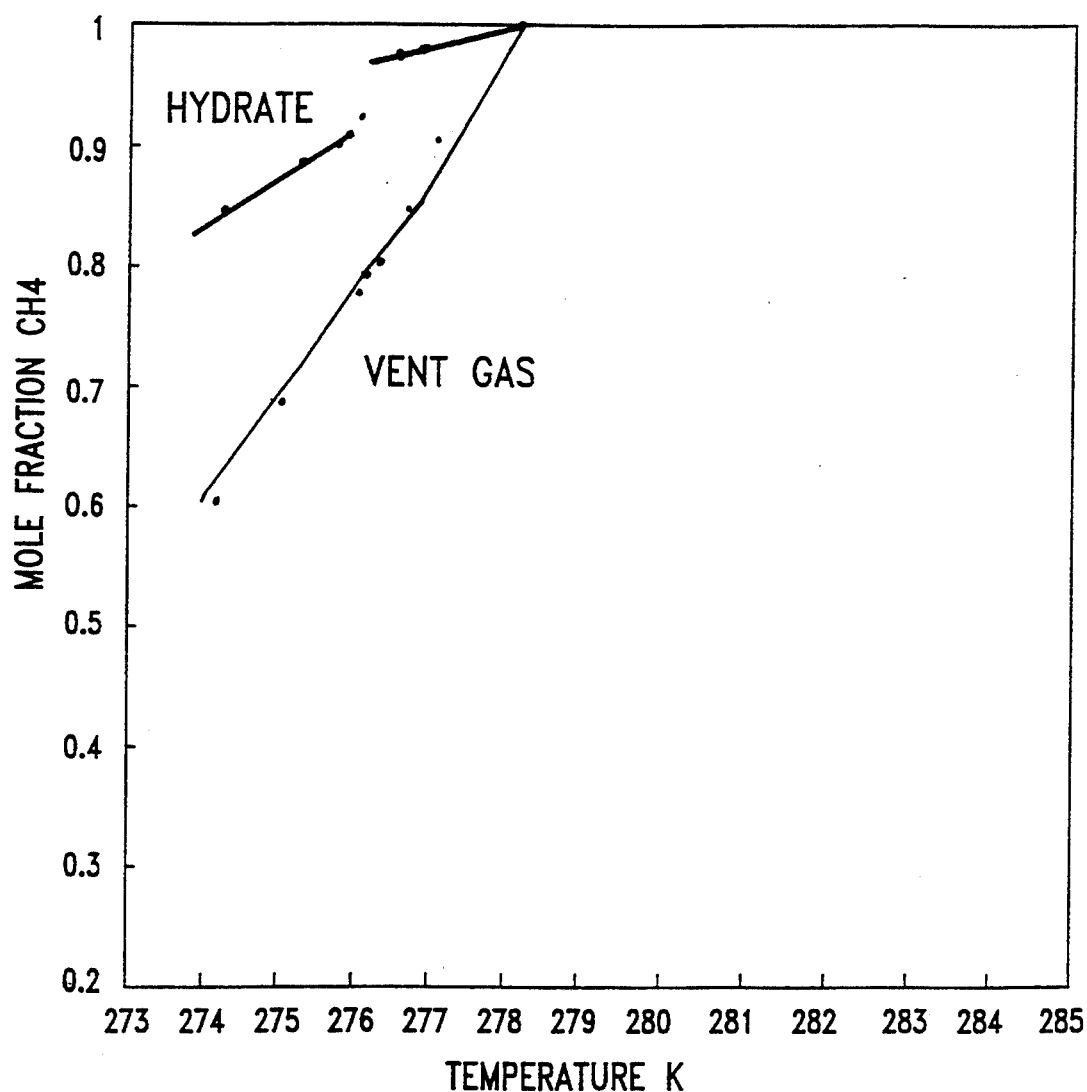
FIG. 7 is a plot of $CH_4$—$N_2$ hydrate equilibrium phase diagram—pressure appx. 660 psia.

The data obtained in these experiments are summarized in FIGS. 5, 6 and 7. There is a much smoother progression of composition over temperature for gas phase equilibrium as compared with that for the hydrate equilibrium phase. The vapor phase composition is in excellent agreement with published data. The abrupt changes in the hydrate composition as temperature is changed have not been documented. It will be noted that in FIG. 3, for example, the hydrate composition is shown to be greater than 95% methane corresponding to a gas vent only slightly above 80%. These changes are attributed difference in hydrate structure. Only several years ago the discovery was made that mixtures of nitrogen and methane can form different structures. These diagrams were used for process analysis. They represent the only available data in this range.

Another series of experiments was conducted at a temperature of around 4° C. and at 820 psia to investigate the dynamics of mixed hydrate formation from mixtures of methane and nitrogen. The speed of impeller 30 was varied from 1500 to 2250 rpm. These results are summarized in Table 2. The rate of hydrate formation was found to increase with impeller speed.

The rate of feed input was then varied from 1333 cc(NTP)/min to 5000 cc(NTP)/min using a 2250 rpm stirring rate. The rate of hydrate formation was relatively high and remained constant over this range. The analysis of the hydrate corresponded to equilibrium values at the temperature and pressure of the system. The analysis of the vent gas varied with flow rate and showed substantial by-passing of inlet gas occurring. Thus operation of this reactor with gas feed exceeding 1500 cc(NTP) results in lower efficiency. Table 3 presents results of these experiments.

A sintered sparger 28 consisting of 60 micron diameter pores in a stainless steel plug was next installed in the hydrate former to enable the dispersed gases to be emitted as finely divided bubbles. Very high rates of hydrate formation, up to 4800 cc(NTP)/min equivalent gas conversion were observed using an inlet feed rate of 5142 cc(NTP)/min.

Further experiments were conducted with a screen sparger 28 with 140 micron size openings and three disk-and-doughnut baffles spaced 1.5 inches apart to reduce possible gas by-passing in the hydrator. Experiments on this modified hydrate forming apparatus demonstrated that high rates of hydrate formation equal to 1,400 cc(NTP)/min could be achieved with the composition of hydrate and corresponding vent gas being close to equilibrium values. There was less than a minute delay time in the initiation of hydrate formation, indicating that the combination of stirring, sparging with 140 micron openings and the disk-and-doughnut baffling 33 is an efficient way to produce hydrates under conditions corresponding to separation of nitrogen-methane mixture. The melting of hydrates suspended in the aqueous phase had not been studied previously by other researchers. To study it presumes that a satisfactory hydrate former 20 is in operation in tandem with the melter 21. Because of the efficient operation of the newly designed former 20 it is possible to study the characteristics of melting hydrates in this manner.

The apparatus described in FIG. 1 was used to demonstrate a continuous operation consisting of a former 20 and melter 21 for single stage contacting of appropriate gas mixtures containing methane and nitrogen. An experiment serving as an example of continuous operation is summarized in Table 4. Hydrate formation was initiated immediately after introducing a 75.91% by volume of methane 24.09% by volume of nitrogen feed gas into the hydrate forming reactor 20. In about 18 minutes, steady state operation of the combined former-melter was achieved and good material balances were observed. Steady state operation was maintained for 60 minutes during which substantial separation was observed.

Further equilibrium experiments were conducted on methanol-water mixtures similar to the previously described experiments using pure methane that we had previously conducted using water alone as the aqueous phase to insure that suitable separation could be obtained using the methanol-water systems. FIG. 6 presents data obtained with a 40 wt. % methanol-water solution at temperatures ranging from 258 to 262K and pressures from 800 to 1400 psia. The data obtained correlated well with thermodynamic predictions involving the effect of methanol on freezing and hydrate formation point lowering. The rates of hydrate formation were very rapid and similar to those obtained for the pure methane-water system.

Figure 9:
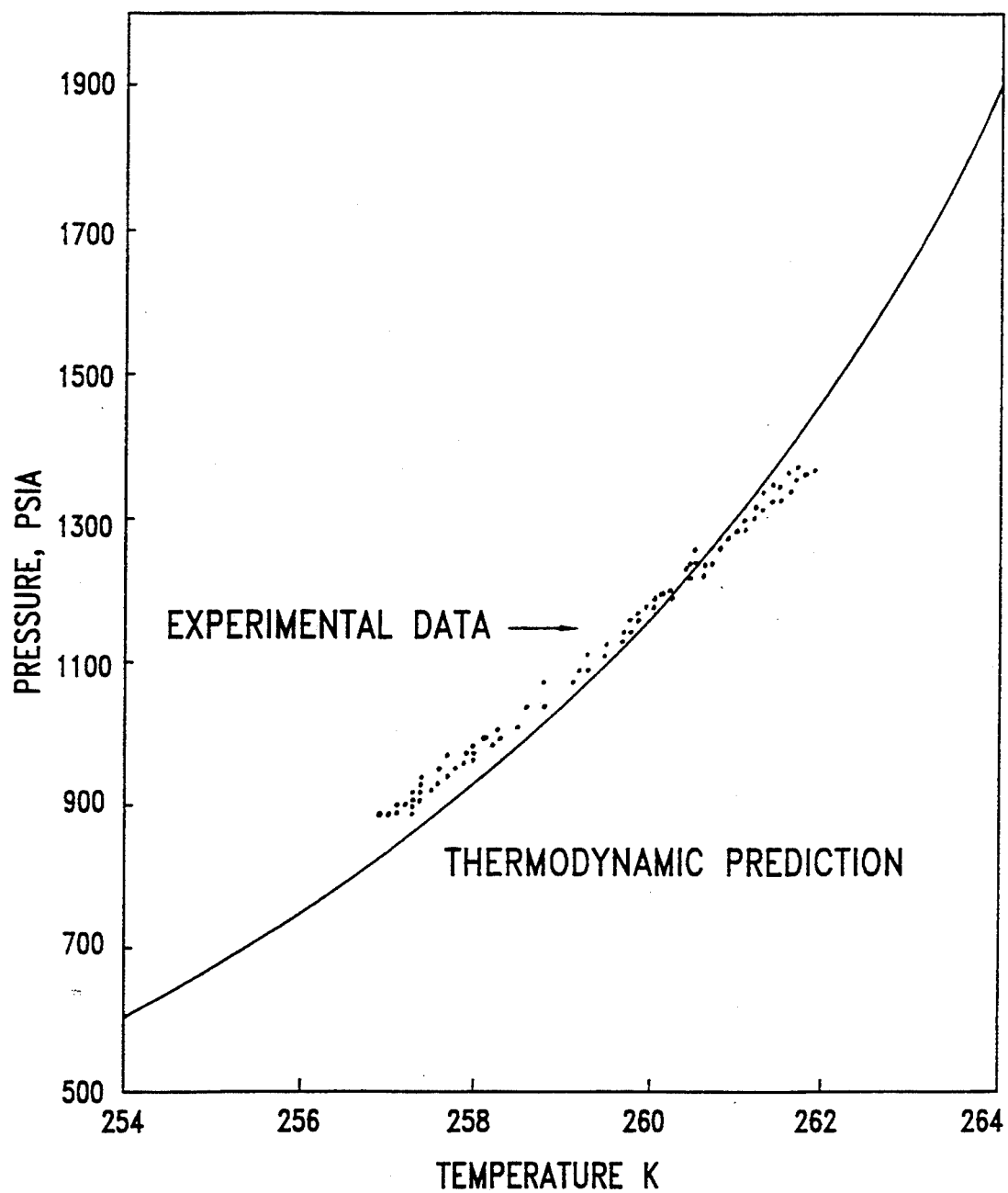
FIG. 9 is a plot of methane hydrate equilibrium data 40 wt. % methanol-water solution.

Additional equilibrium experiments were conducted to study the effect of methanol-water mixtures on the separation of nitrogen and methane. Results were similar to those with pure water and are presented in FIG. 9.

Figure 8:
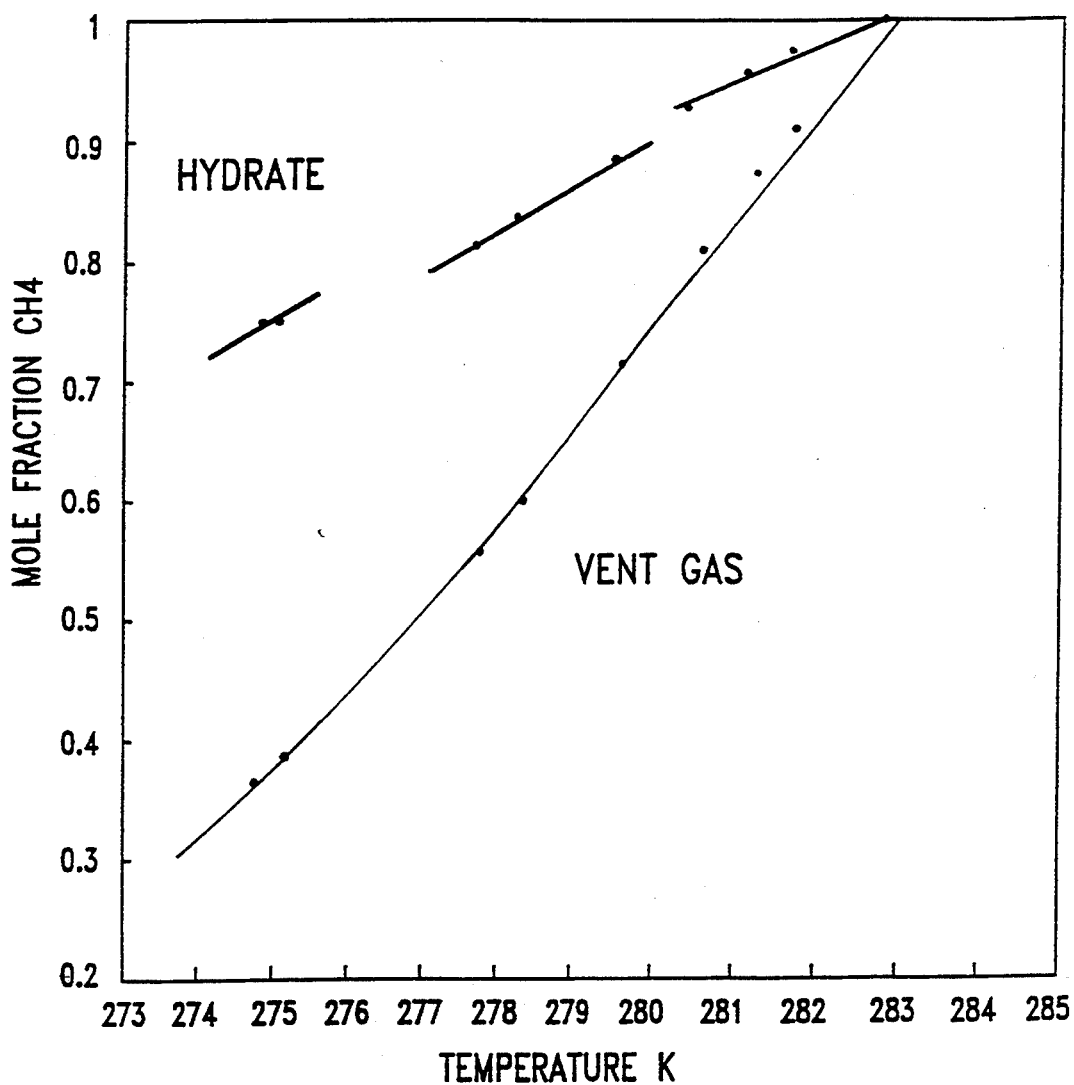
FIG. 8 is a plot of CH$_4$—N$_2$ hydrate equilibrium phase diagram—pressure appx. 1040 psia.

Data of the type shown in FIGS. 6 and 8 can be used to show the effect of methanol addition to water on hydrate formation conditions. In these plots mole fraction of methane is related to the temperature of formation of corresponding hydrate and vent gas composition. For any given methane concentration there will be a temperature difference between the hydrate composition and vent gas composition at a given pressure. Table 5 illustrates the situation for several compositions read from the plots.

It is apparent that the data exhibited in FIG. 8 corresponding to a 40 wt. % by volume methanol-water solution can be conveniently derived from that of pure water shown in FIG. 5. The points in FIG. 8 for a given methane concentration are displaced by those shown in FIG. 6 by a temperature difference which remains constant for both hydrate and vent gas curves. For the hydrate curves the average difference is 25.07° and for the vent gas curves the difference is 24.5° C.

This difference can be related to the hydrate depression temperature. The hydrate depression temperature for methanol as well as other solvent can be related to the molecular weight of the solvent and its mole fraction as presented in a formula given by Nielsen and Bicklin ("Gas Hydrate Control" page 144, vol 24 Encyclopedia of Chem Processing and Design J. McKetta, Marcel Decker, N.Y. 1986). Using this formula for 40 wt. % methanol solution a temperature difference of 22.9° C. is calculated which is not far from the data obtained from FIGS. 6 and 8. The same type of calculations can be made for other solvents by one skilled in the art.

Experiments were conducted to evaluate the performance of other types of devices for gas-liquid mixing to form hydrates. Initially, static experiments were conducted using packed Koch static mixers. A more effective mixing was obtained using Venturi-type devices 40 and 41 shown in FIG. 2. Venturis 40 and 41 with a 0.30 inch diameter throat and three symmetrically spaced injector ports was used to test the efficiency of hydrate production. The apparatus in FIG. 1 was modified to accommodate the installation of the Venturi to replace the sparger 28 and stirrer 31. The Venturi was inserted between the feed chiller 32 and the 1 liter autoclave vessel or former 20. The motive fluid was the cooled aqueous phase liquid leaving the chiller 32. The stream was pressurized to 275 psi above the system operating pressure of 1010 psia. Feed gas was introduced through the three injector ports. The apparatus was operated using the same procedure as previously described.

Rapid hydrate formation occurred. Results were similar to those obtained with the use of stirring and sparging.

Figure 10:
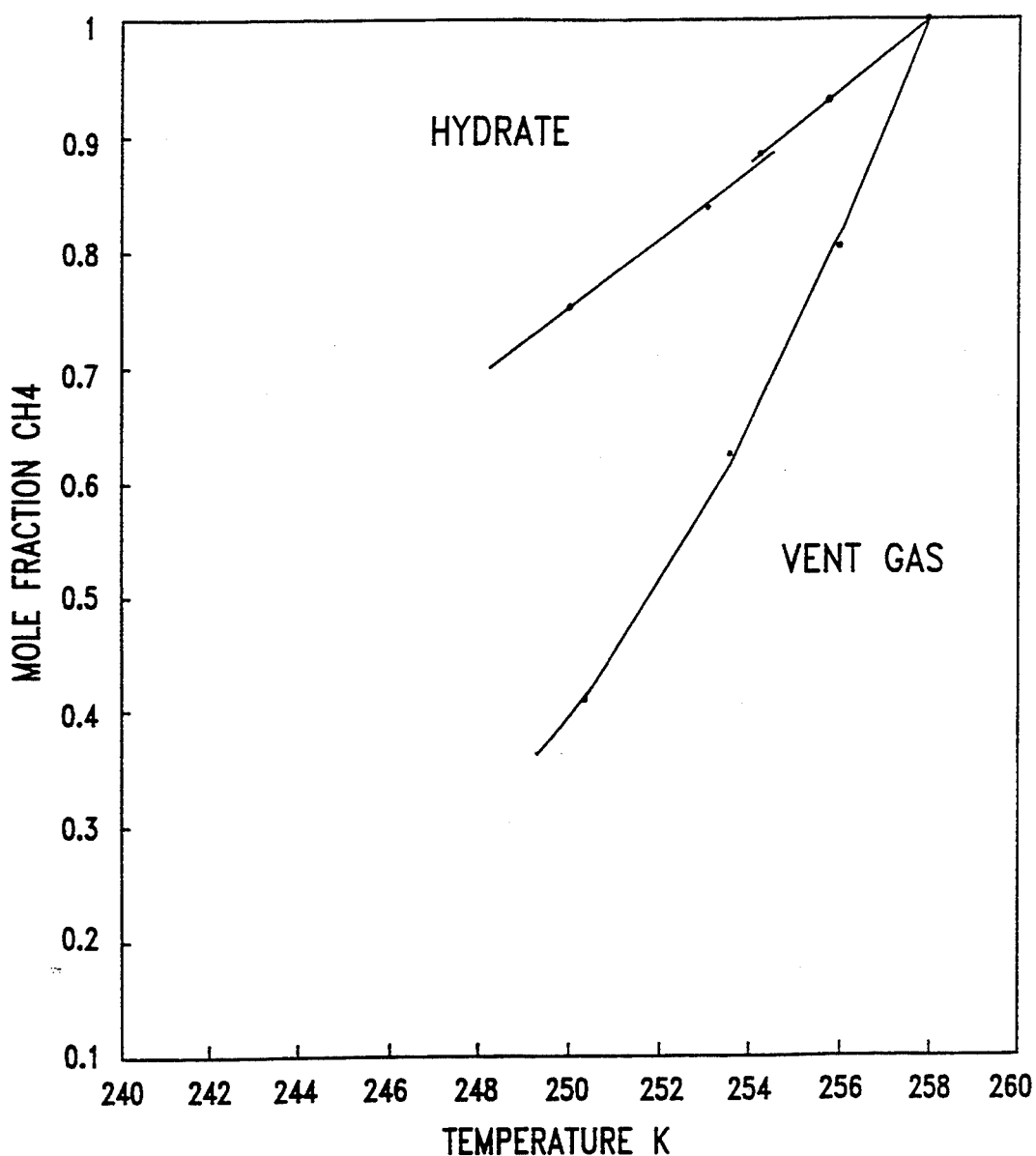
FIG. 10 is a plot of CH$_4$—N$_2$ hydrate equilibrium phase diagram with 40 wt. % methanol-water solution—pressure appx. 1010 psia

The ideas expressed above and the experimental data obtained may be visualized in terms of a separation process involving a countercurrent stagewise contacting of gases and hydrate slurry as shown in FIG. 10 and Table 5. Table 5 illustrates the calculated results for a 75 MMSCFd plant using a 40 wt. % methanol-water solution.

It should be understood that such a series of stages could be used to develop a process sequence such as that illustrated in FIG. 2 entitled, "Hydrate Process for Nitrogen Rejection". This hydrate process operating around 1000 psia involves the formation of mixed nitrogen-methane hydrate from a methanol-water solution and a countercurrent separation of a nominal 25% by volume of nitrogen stream into specification pipeline gas (methane product) corresponding to a maximum nitrogen content of 4 mole % and a reject stream richer in nitrogen with a lower heating value of less than 400 BTU/scf.

A supercooled stream of methanol-water at inlet 41a enters a Venturi mixer 41 and rapidly reacts with the feed gas stream 48 forming a suspension of finely divide dendritic crystals of mixed methane-nitrogen hydrate. This stream is introduced into the nitrogen removal tower 42.

At the top of the tower 42 a supercooled stream of methanol-water at inlet 40a enters a Venturi mixer 40 and rapidly reacts with the nitrogen rich gases drawn from the tower 42 thereby forming a suspension of hydrate crystals. The mixed effluent from the Venturi mixer 40 is introduced into the top 42a of the tower 42. The gaseous stream at exit 42b leaving the top 42a of the tower 42 comprises the product nitrogen rich gas. The suspension moves downward, contacting the gases passing upward from the feed section 42c of the tower 42.

Heat exchangers 43 and 44 serve to heat the suspension as it passes downward, acting as partial reboilers to promote separation of nitrogen from methane. The suspension of hydrate leaving the bottom 42d of the tower 42 corresponds to a hydrate containing a specification methane concentration.

This stream passes to the product melter 44. Exchanger 49 serves to melt the suspended hydrate, producing methane rich product gas at exit 44a. The methanol-water solution may be heated to a sufficiently high temperature to release additional dissolved methane and nitrogen.

The stream leaving the product melter 44 is recycled after chilling. The chiller 50 operates at an intermediate temperature because the lowest temperature is not required to form hydrate from the feed gas. A smaller proportion of the methanol-water stream is further chilled in chiller 51. The effluent from the chiller stream at exit 51a of chiller 51 completes the methanol-water cycle entering the tower 42.

An additional feature of the invention which will complement the use of hydrate alone in gas separation is the simultaneous use of solvents. Thus referring to FIG. 2, the stream from exit 44b of the product melter 44 can contain a high concentration of solvent such as methanol, when depressurized releases a substantial quantity of a gaseous stream rich in methane. This stream may be combined with the product gas stream for exit 44a of the melter 44. This enables the process to operate at a higher throughput for a given solvent circulation.

This additional feature was demonstrated by an experiment in which a high hydrate concentration stream leaving the former 20 of FIG. 1 was isolated in the view port 38 and subsequently slowly decomposed by lowering the pressure to 1 atm. The exit gas, the sum of the gas entrapped in the hydrate, plus the dissolved gas, was analyzed to have a 93.7 vol % methane content. The experiment was conducted at approximate 1010 psia and at 256.8K with a feed gas of 86.7 vol. % methane and 13.3 vol. % nitrogen employing a 40 wt. % methanol-water solution.

Under similar conditions preliminary experiments were conducted to demonstrate the solubility of methane-nitrogen gas in a 40 wt. % methanol-water solution. We obtained an uptake in gas of about 1000 cc(STP)/100 ml of solution.

A survey of the literature was made to establish more exactly the solubility relationships involved. Calculations were made to determine the solubility of a 85 vol. % methane balance nitrogen content gas in equilibrium with a 40 wt % methanol-water solution at 253K and 1000 psia. The Henry's law constant for methane-water was obtained from "Solubility Data Series". Volumes 27, 28, Pergamon Press, Page 3 and calculated to be 10,193 atm. The methane-methanol Henry's law constant was calculated to be 824 atm from Shenderay et.at Gazov, Brom 1961, 6(3), 42–45. The nitrogen-water Henry's law constant was calculated to be 27,987 atm from "Solubility Data Series, Vol. 10 Pergamon Press, page 1. The nitrogen-methanol Henry's law constant was calculated to be 3,632 atm. from "Solubility Data Series" Vol 10, Pregamon Press, page 174. The calculation for mixtures of gases in methanol-water solutions was made by using a formula suggested by Carroll, Chem Eng. Prog., 8 (1972), 55–58. The interaction constant is not used since data by Tokunaga & Kawai, J. Chem. Eng. 8, 1975, 326–327 indicates that it is small. The resulting calculation showed that the dissolved gas corresponds to a methane concentration of 94.6 vol. %. The total gas solubility calculates to 1147 cc(STP)/100 ml of solution. Thus the calculated results confirm the data that was obtained.

The solubilities of methane expressed in terms of the Ostwald absorption coefficients at 25° C. are given in a study by Lannung and Gjoldbaek, Acta Chemica Scandinavics 14, 1124 (1960). The Ostwald coefficient is the volume of gas in milliliters at temperature T and partial pressure p dissolved per unit volume of solvent. For calculations that we have performed, it is convenient to use the Henry's Law constant which is readily related to the Ostwald coefficient. In the following Table 7, we have given both values, L being the Ostwald coefficient. These data show that acetone and ethanol are also promising candidates for use in our hydrate process. Another older investigation by Christopher, J. Phys-Chem 79, 456 (1918) indicates that ethyl ether may also be attractive. An Ostwald coefficient at 20° C. of 1028 is reported corresponding approximately to a Henry's constant, H=215.9 atm. This indicates a solubility of methane in ether that is similar to that of such hydrocarbons as n-hexane and cyclohexene as reported by Lannung-Gjoldbaek in their study. Since either is soluble in water its use in our process could be very attractive in a variation using both hydrate formation and solubility in the aqueous phase.

Given the demonstrated information that hydrates can be formed from the water content of the aqueous phase following predictions of hydrate formation temperature by means of a modification of the Hammerschmidt equation, as discussed above, it is possible to employ other solvents besides methanol with performance that can be predicted on the basis of the thermodynamic calculation.

TABLE 1

RATES OF HYDRATE FORMATION

| Pressure PSIA | Delta T K | CH$_4$ Rate C$_3$H$_8$ Rate cc(NTP)/MIN/ LITER REACTOR |
|---|---|---|
| 1030.7 | 1.93 | 1780 |
| 958.7 | 4.05 | 2879 |
| 784.7 | 1.43 | 1325 |
| 782.7 | 1.71 | 1698 |
| 786.7 | 3.56 | 4724 |
| 736.7 | 3.90 | 3984 |
| 638.7 | 2.16 | 1321 |
| 638.7 | 2.65 | 1893 |
| 705 | 3.7 | 40* |
| | | 800** |

*ESTIMATE FROM DATA OF BISHNOI 9500 CC REACTOR)
**ESTIMATE FROM KNOX PILOT PLANT (10 GAL> REACTOR)

TABLE 2

BATCH HYDRATE FORMING EXPERIMENTS ON THE SEPARATION OF CH4 FROM N2 BY HYDRATE FORMATION EXPERIMENTS VARYING IMPELLER STIRRING SPEED

| RUN NUMBER | 1 | 2 | 3 | 4 |
|---|---|---|---|---|
| FLOW RATE cc(NTP)/min. | | | | |
| INLET | 2307 | 2368 | 2307 | 2307 |
| OUTLET | 1667 | 1795 | 1800 | 1973 |
| HYDRATE FORMATIN cc(NTP)/min | 640 | 573 | 507 | 334 |
| STIRRING SPEED RPM | 2250 | 2000 | 1750 | 1570 |
| CIRCULATION ML/MIN | 860 | 860 | 860 | 860 |
| PRESSURE PSIA | 811.7 | 823.7 | 829.7 | 821.7 |
| TEMPERATURE K | 276.25 | 275.95 | 275.85 | 275.75 |
| COMPOSITION, VOL % CH4 | | | | |
| FEED | 75.96 | 75.96 | 75.96 | 75.96 |
| VENT | 69.51 | 70.70 | 72.00 | 73.40 |
| HYDRATE | 89.05 | 90.75 | 89.00 | 90.70 |

TABLE 3

BATCH HYDRATE FORMING EXPERIMENTS ON THE SEPARATION OF CH4 FROM N2 BY HYDRATE FORMATION EXPERIMENTS VARYING GAS INLET FLOW

| RUN NUMBER | 1 | 2 | 3 | 4 |
|---|---|---|---|---|
| FLOW RATE cc(NTP)/min. | | | | |
| INLET | 1333.3 | 2571.0 | 3461.5 | 5142.9 |
| OUTLET | 757.3 | 1848.0 | 2540.3 | 4232.9 |
| HYDRATE FORMATION cc(NTP)/MIN | 576.0 | 723.0 | 921.2 | 910.0 |
| STIRRING SPEED RPM | 2250 | 2250 | 2250 | 2250 |
| CIRCULATION ML/MIN | 860 | 860 | 860 | 860 |
| PRESSURE PSIA | 821.7 | 823.7 | 833.7 | 823.7 |
| TEMPERATURE K | 276.25 | 276.25 | 276.05 | 276.15 |
| COMPOSITION, VOL % CH4 | | | | |
| FEED | 75.96 | 75.96 | 75.96 | 75.96 |
| VENT | 72.16 | 64.51 | 69.37 | 70.60 |
| HYDRATE | 90.61 | 89.29 | 90.48 | 90.82 |

TABLE 4

TANDEM OPERATION WITH MODIFIED HYDRATOR

| TIME MIN | 12 | 18 | 24 | 32 | 42 | 50 | 60 |
|---|---|---|---|---|---|---|---|
| FEED | | | | | | | |
| FLOW RATE<CC(NTP)/MIN | 2307 | 2307 | 2307 | 2307 | 2307 | 2307 | 2307 |
| COMPOSITION, VOL % CH4 | 75.91 | 75.91 | 75.91 | 75.91 | 75.91 | 75.91 | 75.91 |
| HYDRATOR | | | | | | | |
| PRESSURE, PSIA | 835 | 837 | 841 | 841 | 839 | 839 | 829 |
| TEMPERATURE, °C. | 3.0 | 3.3 | 3.0 | 3.0 | 3.0 | 2.9 | 3.0 |
| VENT GAS, CC(NTP)/MIN | 900 | 740 | 851 | 1052 | 1405 | 1233 | 790 |
| COMPOSITION, VOL 5CH4 | | | | | | | |
| VFNT GAS | 67.73 | 69.21 | 68.51 | 69.32 | 69.01 | 67.77 | 68.42 |
| HYDRATE DEHYDRATOR | | | | | | | |
| PRESSURE, PSIA | 861 | 861 | 859 | 859 | 859 | 859 | 859 |

TABLE 4-continued

| | TANDEM OPERATION WITH MODIFIED HYDRATOR | | | | | | |
|---|---|---|---|---|---|---|---|
| TIME MIN | 12 | 18 | 24 | 32 | 42 | 50 | 60 |
| TEMPERATURE, °C. | | | | | | | |
| HEATER EXIT | 17.0 | 21.6 | 20.1 | 20.5 | 20.3 | 20.2 | 20.0 |
| SETTLER | 7.6 | 7.9 | 7.9 | 7.9 | 7.9 | 7.6 | 8.2 |
| VENT GAS, CC(NTP)/MIN | 1875 | 1125 | 1033 | 838 | 1052 | 1698 | 1671 |
| COMPOSITION, vol % CH4 | | | | | | | |
| VENT GAS | 76.40 | 78.27 | 79.81 | 80.04 | 79.14 | 79.69 | 80.13 |

TABLE 5

TEMPERATURE DISPLACEMENT FOR HYDRATE FORMATION FROM SOLVENTS

| mole % methane | Water | | Water-40 wt % methanol | | Delta temp. | |
|---|---|---|---|---|---|---|
| | Hydrate | Vent | Hydrate | Vent | Hydrate | Vent |
| 0.9 | 225.0 | 257.3 | 280.0 | 281.8 | 25.0 | 24.5 |
| 0.8 | 252.0 | 256.0 | 277.2 | 280.6 | 25.2 | 24.6 |
| 0.75 | 250.3 | 255.5 | 275.00 | 280.0 | 25.0 | 24.5 |
| Average Delta T | | | | | 25.07 | 24.53 |

TABLE 6

HYDRATE PROCESS FOR NITROGEN REJECTION
CAPACITY: 75 MMSCFD
STAGEWISE CALCULATION

| STREAM # | 01 | 11 | 02 | 21 | 31 | 41 | MEOH-H$_2$O |
|---|---|---|---|---|---|---|---|
| MEOH, M LB/MIN | 18.387 | 18.387 | 38.770 | 57.157 | 57.157 | 57.157 | 57.157 |
| H$_2$O, M LB/MIN | 27.580 | 22.284 | 58.155 | 69.266 | 71.197 | 76.588 | 85.735 |
| MEOH WT % | 40.0 | 45.2 | 40.0 | 45.2 | 44.5 | 42.7 | 40.0 |
| TEMP. °F. | −23.8 | −14.2 | −16.4 | −8.9 | −3.9 | 2.4 | 7.4 |
| FLOW GAL/MIN | 5829 | | 12290 | | | | 18119 |
| HYDRATE, LB-MOLES/MIN | 0.000 | 50.295 | 0.000 | 156.402 | 138.068 | 86.874 | 0.000 |
| CH4 VOL % | | 75.0 | | 85.0 | 92.0 | 97.0 | |
| N, VOL % | | 25.0 | | 15.0 | 8.0 | 3.0 | |
| GAS, | N2-VENT | 22 | FEED | 32 | 42 | | PRODUCT |
| LB-MOLES/MIN | 50.295 | 100.589 | 137.170 | 69.538 | 51.194 | | 86.874 |
| CH4 VOL % | 37.0 | 56.0 | 75.0 | 70.0 | 78.5 | | 97.0 |
| N4 VOL % | 63.0 | 44.0 | 25.0 | 30.0 | 21.5 | | 3.0 |
| TEMP. °F. | −14.2 | −8.9 | | −3.9 | 2.4 | | 7.4 |

| SOLUBILITY OF METHANE @ 25° C. | | |
|---|---|---|
| | OSTWALD COEFFICIENT L | HENRY'S CONSTANT H, atm |
| Acetone | 0.616 | 533 |
| Ethanol | 0.534 | 770 |
| Methanol | 0.523 | 1137 |
| Water | 0.0342 | 39,052 |

What is claimed is:

1. A process for separating desired clathrate forming gases from a gas mixture containing the desired clathrate forming gases comprising the steps of providing a gaseous stream of the gas mixture, contacting the gaseous stream with an aqueous solvent to form a solid clathrate hydrate suspension in the aqueous solvent, the forming of the solid clathrate hydrate suspension in the aqueous solvent causing the gaseous stream to be thereafter leaner in the desired clathrate forming gases, and subjecting the solid clathrate hydrate suspension and the aqueous solvent to an elevated temperature and a reduced pressure to produce a product gaseous stream which is richer in the desired clathrate forming gases.

2. A process in accordance with claim 1 in which there is provided a contacting tower and in which there is provided a countercurrent passage of an upwardly moving gas mixture and a downwardly moving stream of the solid clathrate suspension in the aqueous solution in the contacting tower.

3. A process in accordance with claim 1 in which there is provided a melter and the stream of the solid clathrate suspension in the aqueous solution is introduced into the melter in which the solid hydrate suspension decomposes by raising its temperature, releasing the product gas, cooling the aqueous solvent stream, and reintroducing the cooled aqueous stream as feed to the process.

4. A process in accordance with claim 1 in which the clathrate stream after being contacted by the aqueous solvent is decomposed by at least one of raising its temperature and lowering its pressure to effect the release of a gaseous product both by decomposition of the desired clathrate formers and by reduced solubility of the dissolved gases rich in desired clathrate components.

5. A process in accordance with claim 1 in which there is provided a sparger with fine openings used for introducing the gas feed.

6. A process in accordance with claim 5 in which the sparger has fine openings which are less than approximately 140 microns.

7. A process in accordance with claim 1 in which the aqueous solvent comprises at least one of water and in addition any of methanol, ethanol, propanol, acetone, ether, and ethylene glycol mixed with water.

8. A process in accordance with claim 1 in which the gas mixture includes a stream of natural gas and in which a nitrogen stream is separated from the natural gas.

9. A process in accordance with claim 8 in which the natural gas stream contains between 10% and 50% of nitrogen by volume and the remainder thereof predominantly methane, the natural gas stream being contacted with an aqueous solvent mixture at a pressure of between approximately 500 to 3,500 psia and at temperatures above the freezing point of the aqueous solvent mixture.

10. A process in accordance with claim 1 in which the gas mixture is a stream of natural gas.

11. A process in accordance with claim 10 in which ethane, propane, isobutane, and 4-butane are separated from other natural gas components which form clathrates less readily.

12. A process in accordance with claim 10 in which the natural gas stream contains at least 5% by volume of hydrocarbons forming hydrates related to methane, including ethane, propane, isobutane, and n-butane and in which additional stages of separation are provided so that these components are progressively separated from the methane rich production stream.

13. A process in accordance with claim 1 in which the gas mixture includes carbon dioxide and hydrogen sulfide to provide a gas stream for formation of hydrates rich in these substances.

14. A process in accordance with claim 10 in which the natural gas stream contains in addition to hydrocarbon components the acid gases hydrogen sulfide and carbon dioxide, which includes the provision of additional hydrate separation stages to separate these components from the methane rich product stream.

15. A process in accordance with claim 1 in which the stream of the gas mixture is rich in carbon monoxide and hydrogen containing methane and is contacted with an aqueous solvent to produce a product stream comprising at least 90% by volume of methane and a reject gas containing hydrogen and at least 90% by volume of the carbon monoxide of the feed stream.

16. A process in accordance with claim 1 in which the stream of the gas mixture is rich in carbon dioxide and predominate methane and is contacted with an aqueous solvent to produce a product stream comprising at least a 90% by volume of carbon dioxide stream and a reject gas containing at least a 90% by volume of a methane stream.

17. A process in accordance with claim 1 in which the aqueous solvent stream is depressurized in order to remove dissolved gas as an additional product.

18. A process in accordance with claim 17 in which the dissolved gas as an additional product is reintroduced for recirculation.

19. A process in accordance with claim 1 in which intimate mixing is provided by external mixers including at least one of turbo-agitators, static mixers, impinging jets, stirring mixers, spargers and Venturi jet mixers.

20. A process in accordance with claim 1 in which the aqueous solvent contains methanol, ethanol, propanol, acetone, ether or ethylene glycol mixed with water.

21. A process in accordance with claim 10 in which a nitrogen stream is separated from natural gas.

22. A process in accordance with claim 10 in which a natural gas stream containing between 10% and 50% by volume of nitrogen and the balance predominantly methane is contacted with an aqueous solvent mixture at a pressure of 500 to 3,500 psia and at a temperature above the freezing point of the aqueous solution.

23. A process in accordance with claim 10 in which ethane, propane, isobutane, and 4-butane are separated from other natural gas components that form clathrates readily.

24. A process in accordance with claim 10 in which the natural gas stream contains at least 5% by volume of hydrocarbons forming hydrate more relative to methane including ethane, propane, isobutane, and n-butane and in which additional stages of separation are provided in order that the components are progressively separated from the methane rich product stream.

25. A process in accordance with claim 10 in which the natural gas stream contains in addition to hydrocarbon components, the acid gases hydrogen sulfide and carbon dioxide and in there is which included the provision of additional hydrate separation stages to separate these components from a methane rich product stream.

26. A process in accordance with claim 10 in which at least one of carbon dioxide and hydrogen sulfide are separated from natural gas by formation of hydrates rich in these substances.

27. A process in accordance with claim 19 in which additional mixing is provided by passing the effluent from the Venturi jet mixer through a static mixer.

28. A process in accordance with claim 1 in which a stream is separated from gas produced in a gas synthesis process.

29. A process in accordance with claim 28 in which a stream rich in carbon monoxide and hydrogen is separated from methane produced in a gas synthesis process.

* * * * *